(12) United States Patent
Meadows et al.

(10) Patent No.: US 11,638,797 B2
(45) Date of Patent: May 2, 2023

(54) APPARATUS FOR ENABLING BLIND ENDOTRACHEAL TUBE OR GUIDE WIRE INSERTION INTO THE TRACHEA

(71) Applicant: AIRWAY MANAGEMENT SOLUTIONS, LLC, Raleigh, NC (US)

(72) Inventors: Robert Michael Meadows, San Antonio, TX (US); Rocco Carl Conca, Raleigh, NC (US); Uriah Shane Popp, Havre de Grace, MD (US)

(73) Assignee: AIRWAY MANAGEMENT SOLUTIONS, LLC, Raleigh, NC (US)

( * ) Notice: Subject to any disclaimer, the term of this patent is extended or adjusted under 35 U.S.C. 154(b) by 342 days.

(21) Appl. No.: 16/826,161

(22) Filed: Mar. 20, 2020

(65) Prior Publication Data

US 2020/0297958 A1    Sep. 24, 2020

Related U.S. Application Data

(60) Provisional application No. 62/822,041, filed on Mar. 21, 2019.

(51) Int. Cl.
*A61M 16/04*        (2006.01)

(52) U.S. Cl.
CPC .... *A61M 16/0488* (2013.01); *A61M 16/0411* (2014.02); *A61M 16/0418* (2014.02); *A61M 2210/0625* (2013.01); *A61M 2210/105* (2013.01); *A61M 2210/1032* (2013.01)

(58) Field of Classification Search
CPC .......... A61M 16/0411; A61M 16/0488; A61M 2210/1032; A61M 2210/105
See application file for complete search history.

(56) References Cited

U.S. PATENT DOCUMENTS 4,672,960 A * 6/1987 Frankel ............. A61M 16/0415
                                                        128/207.14
4,774,949 A * 10/1988 Fogarty ................ A61M 25/01
                                                        606/108

(Continued)

FOREIGN PATENT DOCUMENTS

| GB | 2096467 A * | 10/1982 | ......... A61B 1/00098 |
| WO | WO-02092144 A2 * | 11/2002 | ............ A61M 16/04 |
| WO | WO-2010017685 A1 * | 2/2010 | ........ A61M 16/0409 |

*Primary Examiner* — Kathryn E Ditmer
(74) *Attorney, Agent, or Firm* — Outlier Patent Attorneys, PLLC

(57) ABSTRACT

An intubation assistance device facilitates insertion of an endotracheal tube or a guide wire into a patient's trachea without requiring a laryngoscope. The device includes a curved flexible tubular member that has a proximal portion having a proximal end, a distal portion having a distal end, and a curved portion between the proximal portion and the distal portion. A lumen extends from the proximal end of the tubular member and terminates in the curved portion of the tubular member. The lumen is sized and shaped so that an endotracheal tube and/or a guide wire is axially moveable through the lumen. A ramp is disposed at a distal end of the lumen, and is angled to facilitate insertion of the endotracheal tube and/or guide wire into the patient's trachea. The distal portion of the tubular member includes an esophageal protrusion that is configured to be inserted in the patient's esophagus.

20 Claims, 7 Drawing Sheets

(56) References Cited

U.S. PATENT DOCUMENTS

| | | | | |
|---|---|---|---|---|
| 4,905,667 | A * | 3/1990 | Foerster | A61M 25/09 600/113 |
| 5,259,371 | A * | 11/1993 | Tonrey | A61M 16/04 128/207.14 |
| 5,339,805 | A * | 8/1994 | Parker | A61M 16/0409 128/207.14 |
| 5,720,275 | A * | 2/1998 | Patil | A61M 16/0418 128/207.14 |
| 5,791,341 | A * | 8/1998 | Bullard | A61M 16/0445 128/207.18 |
| 5,819,733 | A * | 10/1998 | Bertram | A61M 16/0459 128/207.14 |
| 6,095,144 | A * | 8/2000 | Pagan | A61M 16/0418 128/207.14 |
| 6,378,521 | B1 * | 4/2002 | Van Den Berg | A61M 16/0409 128/207.14 |
| 7,040,312 | B2 * | 5/2006 | Alfery | A61M 16/0409 128/207.14 |
| 2001/0054425 | A1 * | 12/2001 | Bertram | A61M 16/0415 128/207.14 |
| 2008/0078402 | A1 * | 4/2008 | Mongeon | A61M 16/0436 128/207.14 |
| 2009/0101140 | A1 * | 4/2009 | Miller | A61M 16/04 128/200.26 |
| 2011/0146690 | A1 * | 6/2011 | Wood | A61M 16/04 128/207.14 |
| 2012/0234328 | A1 * | 9/2012 | Bertram | A61M 16/0493 128/207.15 |
| 2017/0216545 | A1 * | 8/2017 | Avitsian | A61M 16/0488 |
| 2019/0054266 | A1 * | 2/2019 | Sun | A61M 16/0447 |
| 2020/0114105 | A1 * | 4/2020 | Molnar | A61B 1/053 |

* cited by examiner

APPARATUS FOR ENABLING BLIND ENDOTRACHEAL TUBE OR GUIDE WIRE INSERTION INTO THE TRACHEA

CROSS-REFERENCE TO RELATED APPLICATIONS

This application claims priority to claims benefit of U.S. Provisional Application No. 62/822,041, filed on Mar. 21, 2019, entitled "APPARATUS FOR ENABLING BLIND BOUGIE INSERTION INTO THE TRACHEA." That application is hereby incorporated by reference herein in its entirety.

BACKGROUND

Field of the Art

This disclosure relates to medical devices. More specifically, the present disclosure relates to human airway management systems.

Discussion of the State of the Art

Endotracheal tubes are commonly used for managing and ventilating the airways of patients who have stopped breathing. In order to establish a definitive airway, the endotracheal tube is placed in the trachea with a cuff inflated below the vocal cords. However, placing endotracheal tubes into the patient's trachea is no easy task. It involves passing an endotracheal tube into the trachea under direct laryngoscopy, a procedure that requires significant skill and experience to practice consistently and reliably. Even for skilled practitioners, success rates are low for proper intubation in a first attempt. In many hospital and lab settings, it is not feasible to provide and maintain the education and skill set needed for practitioners to be proficient at intubations. Additionally, at nighttime or in rural locations, advance airway providers, who are skilled and experienced in proper intubation techniques, may not be readily available.

Moreover, according to traditional endotracheal tube placement procedures, once an endotracheal tube (hereinafter also referred to as "ET tube") is placed into a patient, tube placement must be verified. This multi-step verification process often creates delays in applying chest compressions and radiographic imaging, which may be necessary or critical in saving a patient's life.

Sometimes, as a result of unavailability of skilled practitioners or the delay caused by traditional ET tube placement methodologies, some patients do not receive proper intubations. Instead, medical professionals often begin ventilating patients with a bag valve mask (BVM) until a more experienced provider arrives to secure a more definitive airway. BVM, however, sometimes does more harm than good. The problem with BVMs is that in providing positive pressure, BVM ventilations ventilate not only the lungs, but also force air into the stomach, often leading to gastric inflation and subsequent emesis. This greatly increases the change of aspiration of stomach contents into the lungs, which can significantly compromise the patient's prognosis.

As an alternative to establishing a definitive airway, supraglottic airway devices are used for advanced airway management. Supraglottic airway devices isolate and ventilate above the glottic opening. As such, supraglottic airway devices keep the upper airway open and use positive-pressure ventilation, but do not establish a definitive airway. Although supraglottic airway devices may be easier to use and require less training than placing an ET tube under direct laryngoscopy, they are not without complications. For example, in some cases, supraglottic airway devices have been shown to provide inadequate ventilation and are ineffective for patients with upper airway edema.

What is needed is a reliable, easy to use apparatus for establishing a definitive airway.

SUMMARY

The present invention overcomes the challenges described above with a device that can be used to place a bougie (or a guide wire) or ET tube into a patient's trachea. The device does not require the aid of laryngoscope, and can be used by professionals who are not specifically trained in ET tube placement methodologies.

The present invention accomplishes these objective by using a lumen that, when inserted into a patient's mouth without the aid of a laryngoscope, travels past the oropharynx and seats itself within the hypopharynx. The device is further comprised of a ramp that extends beyond the lumen at an angle greater than 90 degrees. When a guide wire or ET tube is placed within the lumen, it travels to the ramp and becomes placed in the trachea. As such, the present invention enables users to place a guide wire or ET tube into the trachea without the aid of an imaging device and enables users who are not specifically trained in ET tube placement to perform intubation.

As such, the present invention significantly reduces the complexity and costs associated with training and staffing airway specialists. Moreover, the present invention enables users to provide a reliable airway to patients who are in urgent or critical need.

BRIEF DESCRIPTION OF THE DRAWING FIGURES

The accompanying drawings illustrate several embodiments and, together with the description, serve to explain the principles of the invention according to the embodiments. It will be appreciated by one skilled in the art that the particular arrangements illustrated in the drawings are merely exemplary and are not to be considered as limiting of the scope of the invention or the claims herein in any way.

FIG. 1 illustrates an apparatus of the present invention in accordance with an embodiment of the invention.

FIG. 2 also illustrates an apparatus of the present invention in accordance with an embodiment of the invention.

DETAILED DESCRIPTION

Figure 1:
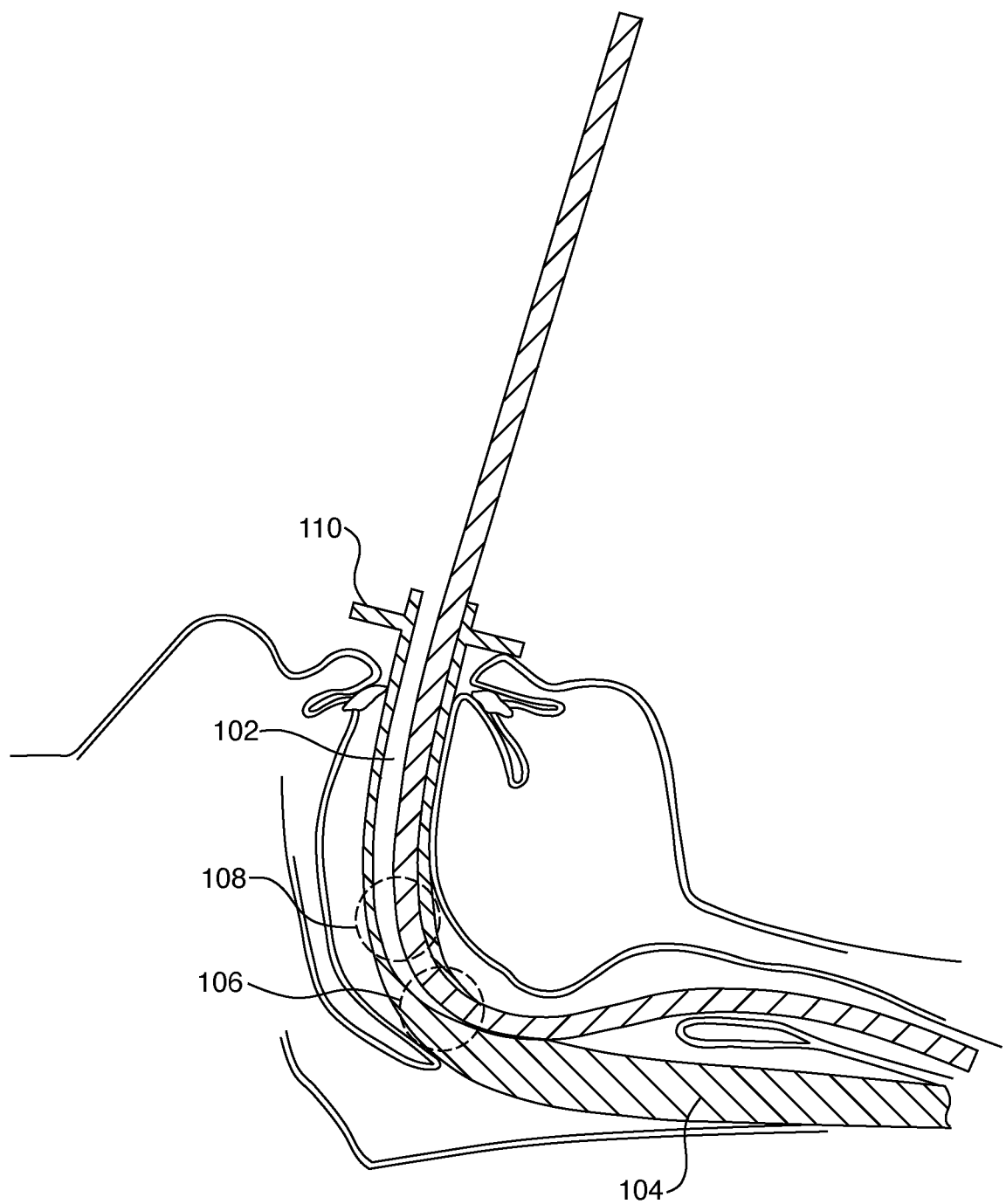

The apparatus of the present invention is for enabling blind insertion of an endotracheal tube (ET tube) or a guide wire into a patient's trachea. In one embodiment, the apparatus comprises a lumen comprising a distal and a proximal end, the lumen for insertion into a patient's mouth, wherein the distal end of the lumen is seated within the patient's hypopharynx when the lumen is placed into the patient, a ramp disposed near the distal end of the lumen, the ramp enabling a guide wire to be placed directly into the patient's trachea, the ramp having an opening that forms an approximately 100 degree angle with the lumen, a curved portion disposed within the lumen for guiding the distal end of the lumen into the patient's hypopharynx when the lumen is inserted into the patient's mouth, and a guide member disposed near the proximal end of the lumen, the guide member notifying a user that the distal end of the lumen is seated within the patient's hypopharynx.

In another embodiment, the apparatus includes a lumen having a distal end and a proximal end. The lumen is sized and shaped to accommodate an ET tube. The distal end of the lumen is coextensive with a wedge-shaped protrusion that is configured to pass through the vocal cords when the apparatus is completely inserted. Below the wedge-shaped protrusion is an esophageal protrusion that is configured to be seated within the patient's esophagus when the device is fully inserted. Between the wedge-shaped protrusion and the esophageal protrusion is a gap that is configured to accommodate the junction between the esophagus and the vocal cords. For example, the gap has a V-shaped surface that may be in contact with the arytenoid, such as the arytenoid cartilage, arytenoid muscles, and/or the interarytenoid notch. The apparatus further includes a foot or spacer that pushes against the patient's hypopharynx to ensure that the protrusions are correctly positioned in the vocal cords and the esophagus.

Various embodiments of the inventive apparatus, system, and method are disclosed herein, including numerous alternative arrangements. However, it should be appreciated that these are presented for illustrative purposes only and are not limiting of the embodiments contained herein or the claims presented herein in any way. One or more of the arrangements may be widely applicable to numerous embodiments, as may be readily apparent from the disclosure. In general, arrangements are described in sufficient detail to enable those skilled in the art to practice one or more of the embodiments, and it should be appreciated that other arrangements may be utilized and that structural, logical, software, electrical and other changes may be made without departing from the scope of the embodiments. Particular features of one or more of the embodiments described herein may be described with reference to one or more particular embodiments or figures that form a part of the present disclosure, and in which are shown, by way of illustration, specific arrangements of one or more of the aspects. It should be appreciated, however, that such features are not limited to usage in the one or more particular embodiments or figures with reference to which they are described. The present disclosure is neither a literal description of all arrangements of one or more of the embodiments nor a listing of features of one or more of the embodiments that must be present in all arrangements.

Headings of sections provided in this patent application and the title of this patent application are for convenience only and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an aspect with several components in communication with each other does not imply that all such components are required. To the contrary, a variety of optional components may be described to illustrate a wide variety of possible embodiments and in order to more fully illustrate one or more embodiments. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the embodiments, and does not imply that the illustrated process is preferred. Also, steps are generally described once per aspect, but this does not mean they must occur once, or that they may only occur once each time a process, method, or algorithm is carried out or executed. Some steps may be omitted in some embodiments or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other embodiments need not include the device itself.

Techniques and mechanisms described or referenced herein will sometimes be described in singular form for clarity. However, it should be appreciated that particular embodiments may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of various embodiments in which, for example, functions may be executed out of order from that shown or discussed, including substantially concurrently or in reverse order, depending on the functionality involved, as would be understood by those having ordinary skill in the art.

System Overview

Figure 2:
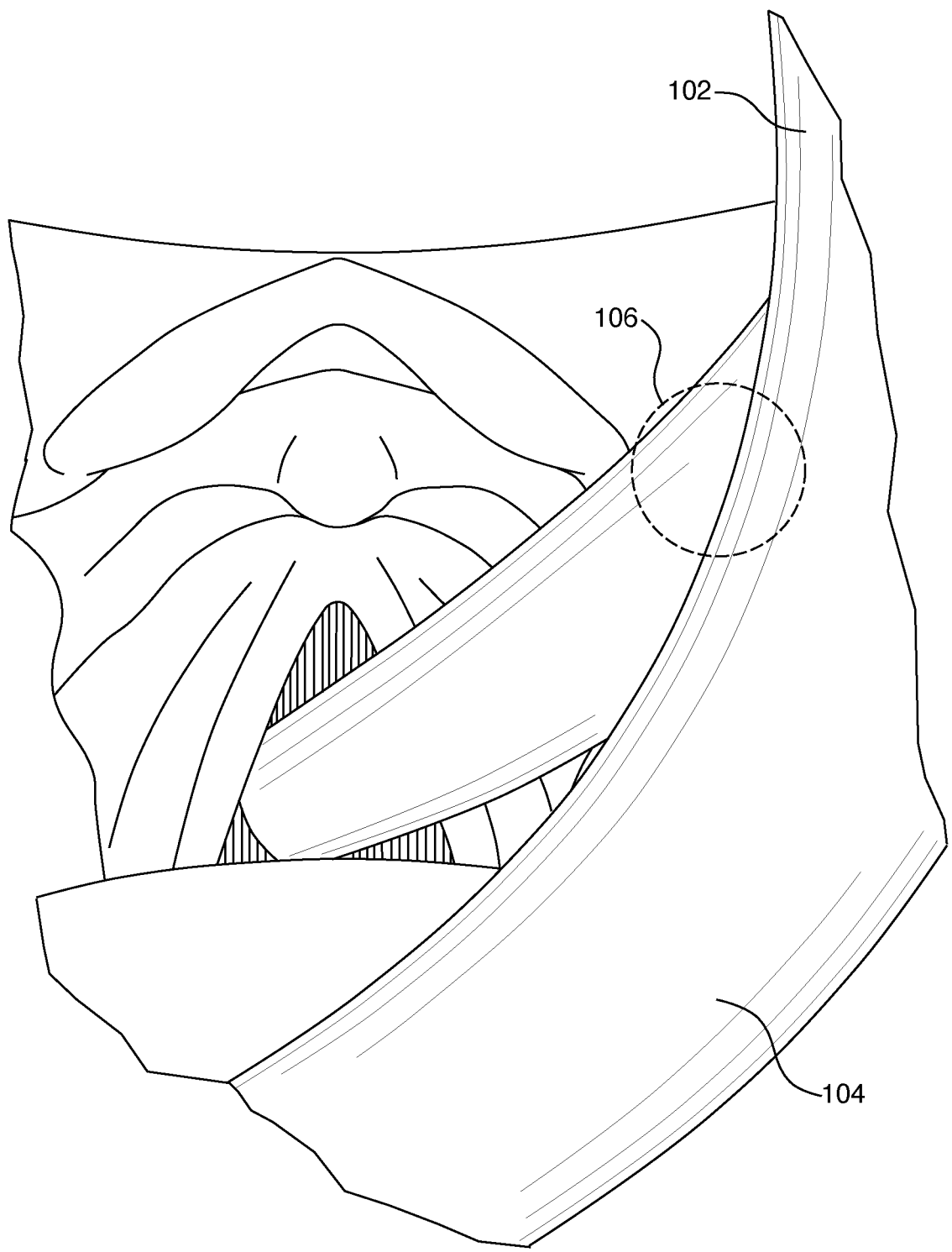
Figure 3A:
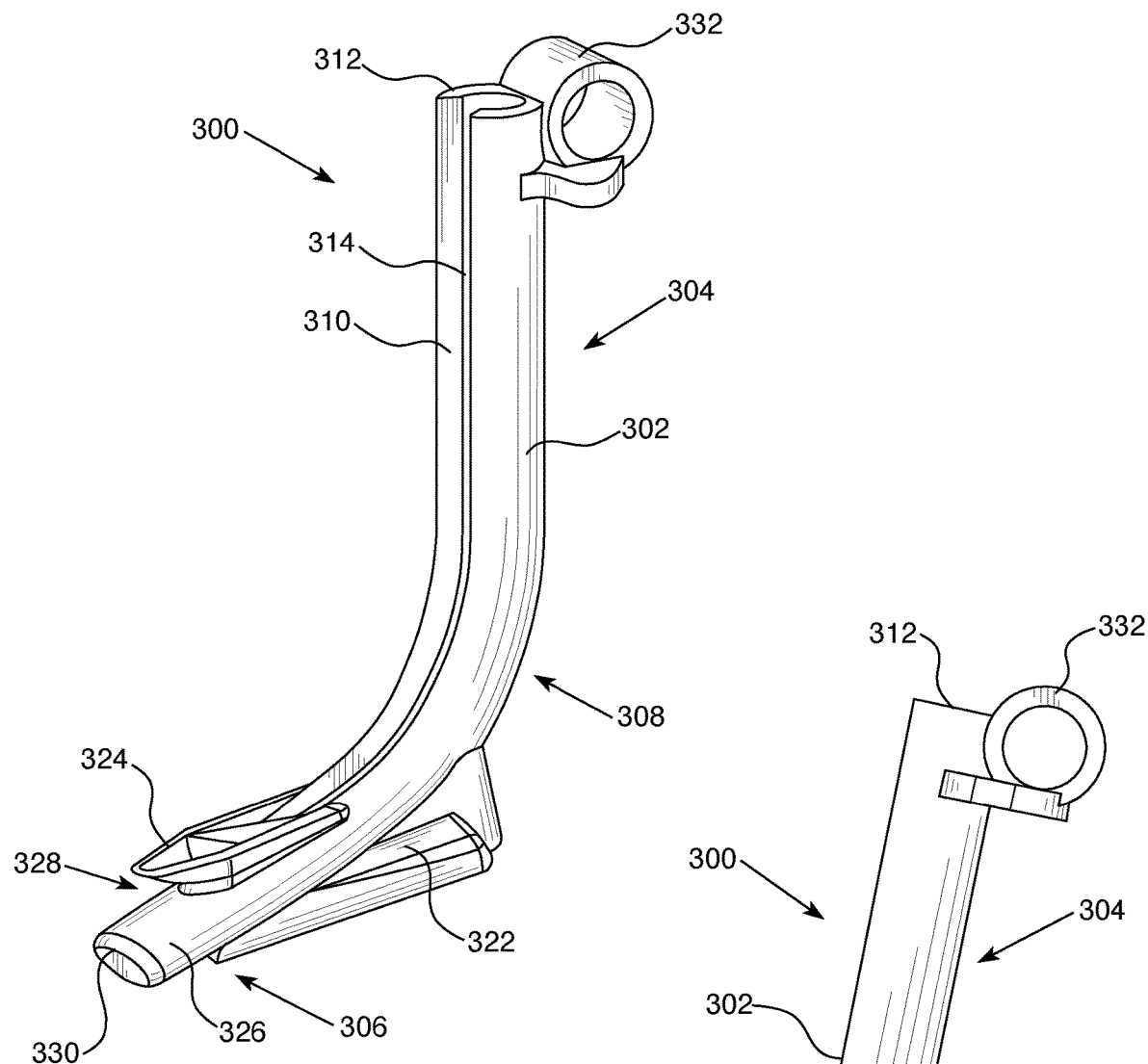
FIGS. 3A-3E are perspective, side, front, top, and close-up views, respectively, of an apparatus of the present invention in accordance with another embodiment of the invention.
Figure 3B:
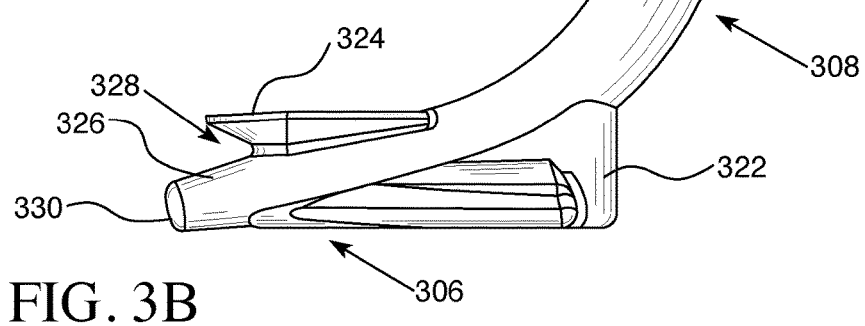
Figure 3C:
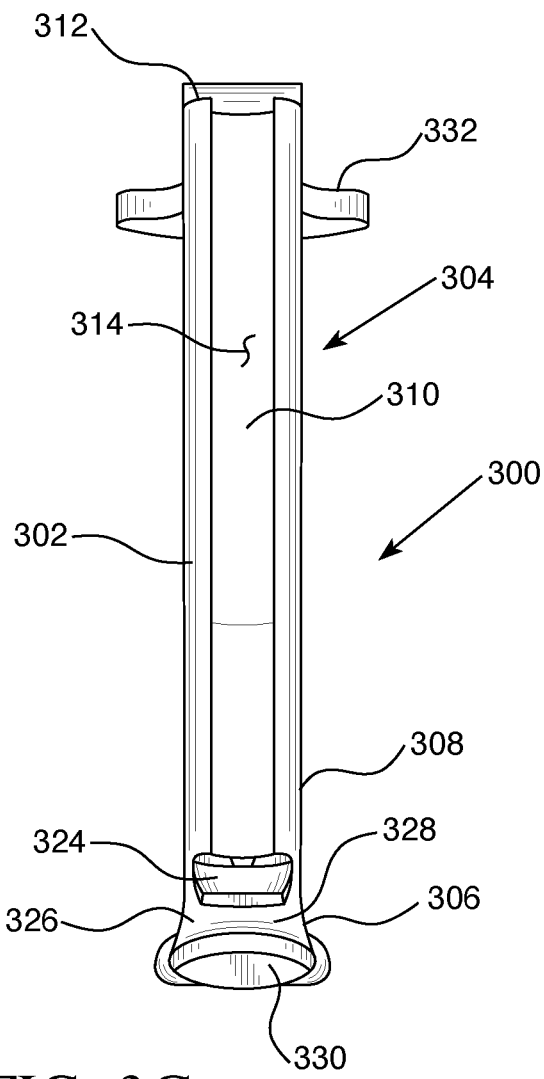
Figure 3D:
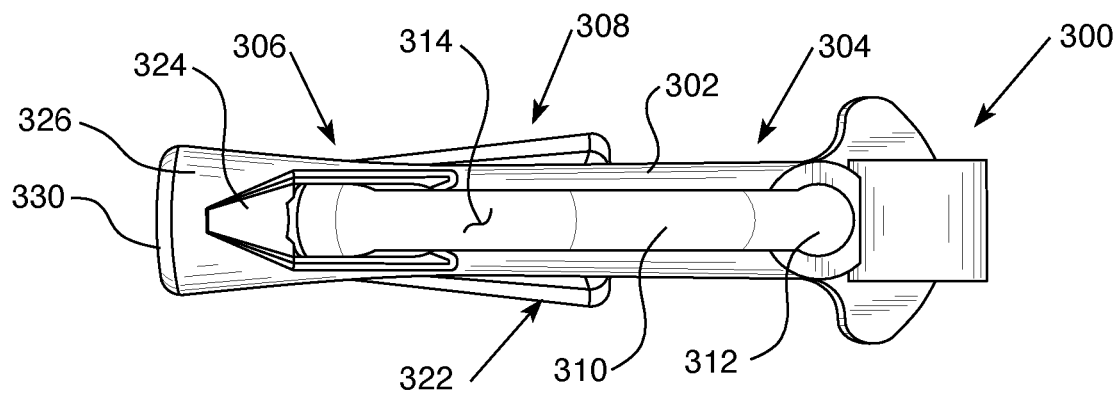
Figure 3E:
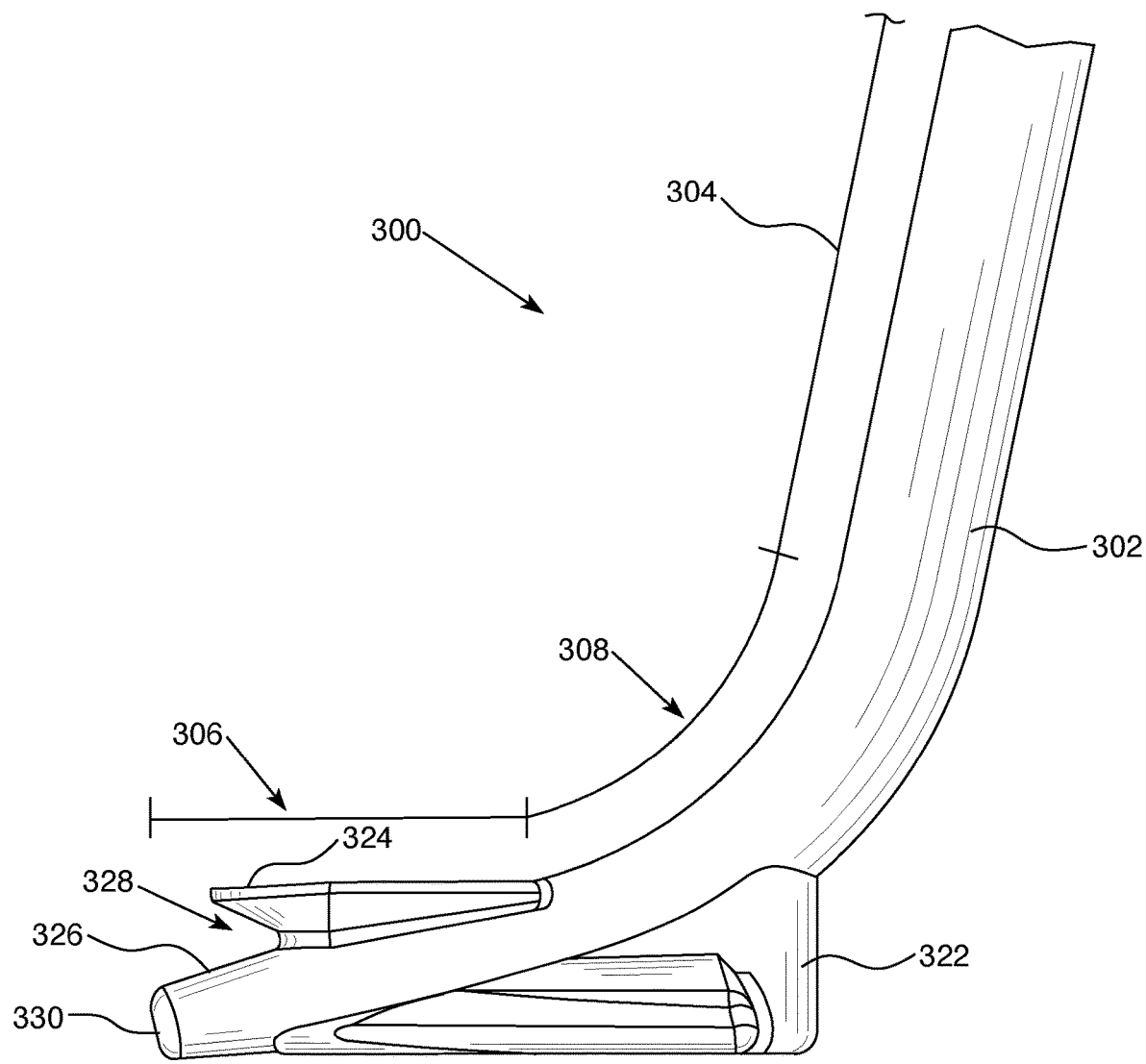

FIGS. 1 and 2 illustrate the inventive apparatus in accordance with an embodiment of the invention. It is comprised of a lumen 102, an expansion member 104, a ramp 106, a flexible curved portion 108, and a guide member 110. The apparatus shown in FIGS. 1 and 2 is an exemplary embodiment of the invention. However, the present invention is not intended to be limited to this particular embodiment. Alternatives, in accordance to the description provided herein, including those that would be readily apparent to a person or ordinary skill in the art are also encompassed in the present disclosure.

Lumen

The lumen 102, in accordance with one embodiment of the invention, is for placing in a patient's mouth. When placed in such a manner, the lumen 102 extends from the patient's mouth, extends past the patient's oropharynx, and seats itself within the patient's hypopharynx. In one embodiment, the lumen 102 may be comprised of an elongated hollow tube of medical grade plastic having a flexible or semi-flexible shape.

In one embodiment of the invention, the lumen 102 has an interior diameter that is at least large enough to accommodate a guide wire such as a bougie. In one embodiment of the invention, the lumen 102 may be comprised of an interior compartment that subdivides the lumen 102 into two lumens. In such an embodiment, at least one interior compartment may specifically guide the guide wire to the ramp, as disclosed further below. In this configuration, the guide wire lumen/compartment may have an interior diameter that is larger than the exterior diameter of the guide wire.

Expansion Member

In one embodiment of the invention, the expansion member 104 is disposed at the distal end of the lumen 102. In one embodiment of the invention, the expansion member 104 seals the esophagus, or at least fits snugly over a patient's laryngeal inlet when in use. The expansion member 104 may have an opening that is co-extensive with the internal portion of the lumen 102. The interior diameter of the expansion member 104 and the lumen 102 may be generally constant, but the diameter of the expansion member 104 is greater than the exterior diameter of the lumen 102.

Ramp

In one embodiment of the invention, a ramp 106 is disposed near the distal end of the lumen 102 and proximal to the expansion portion 104. The ramp 106, as illustrated in FIGS. 1 and 2, extends beyond the lumen 102 at an angle greater than 90 degrees. In one embodiment, the ramp 106 extends at an approximately 100 degree angle from the lumen 102. The specific angle at which the ramp 106 extends from the lumen 102 may vary, as would be readily apparent to a person of ordinary sill in the art, without departing from the scope of the invention so long as the ramp enables a guide wire or a bougie to enter the trachea, or more specifically, the rima glottidis, which may be surrounded by vocal folds on either side.

In one embodiment of the invention, the ramp 106 is curved. The specific curvature of the ramp 106 may vary, as would be readily understood by a person of ordinary skill in the art, without departing from the scope of the invention to the extent that the ramp 106 enables a guide wire or a bougie to enter the trachea.

In one embodiment, the interior diameter of the ramp 106 is greater than the exterior diameter of a guide wire or a bougie. This feature of the present invention permits a guide wire to safely pass through the lumen 102, through the ramp 106, and into the trachea. An ET tube may be passed over the bougie to complete the intubation process.

Flexible Curved Portion

The lumen 102 of the present invention may be comprised of a flexible or a semi-flexible curved portion 108 that enables the lumen 102 to properly travel past the patient's oropharynx and to the patient's hypopharynx. In one embodiment of the invention, the curved portion 108 may enable the lumen 102 to take the same shape as the curve formed by the interior portions of the patient's nasopharynx, oropharynx, and hypopharynx. Moreover, the curved portion 108 is flexible, which enables it to take a variety of different shapes to accommodate a variety of different patients and the dimensions of their interior organs and structures.

Guide Member

The guide member 110 may be disposed along the proximal end of the lumen 102. The guide member 110 may provide an indication to a user that the lumen 102 has reached the patient's trachea. In one embodiment of the invention, the guide member 110 may be indications or indentations disposed along the lumen 102, which may passively notify or alter a user to stop inserting the lumen 102 further into the patient. In one example, when an indication or indentation on the guide member 110 reaches the patient's teeth, that may represent an indication that the user should stop inserting the lumen 102 into the patient because the distal end of the lumen 102 has reached the patient's trachea. The specific design and the number of guide members 110 that may be disposed along the lumen 102 may vary, as would be readily apparent to a person or ordinary skill in the art, without departing from the scope of the invention to the extent that the guide member 110 passively guides a user as to whether to continue inserting the lumen 102 into a patient or to stop.

An intubation assistance device 300 in accordance with another embodiment of the present invention is depicted in FIGS. 3A-3E. In general, the device 300 is configured to be introduced through the mouth of a patient, and passed through the oropharynx and hypopharynx until the distal end of the device 300 is positioned in the esophagus, in the vocal cords, and contacts the arytenoid. As such, the distal end of the device 300 is shaped to have a first protrusion that fits in the vocal cords, a second protrusion that fits in the esophagus, and a space between the two protrusions that accommodates the junction between the esophageal opening and the vocal cords. For example, the space between the protrusions has a V-shaped surface that may be in contact with the arytenoid, such as the arytenoid cartilage, arytenoid muscles, and/or the interarytenoid notch.

The intubation assistance device 300 includes a curved, flexible tubular member 302 that has a proximal portion 304, a distal portion 306, and a curved portion 308 between the proximal portion 304 and the distal portion 306. The tubular member 302 is made of medical grade plastic, and is flexible or semi-flexible. The curved portion 308 may enable the tubular member 302 to take the same shape as the curve formed by the interior portions of the patient's nasopharynx, oropharynx, and hypopharynx. Moreover, the tubular member 302 is flexible, which enables it to take a variety of different shapes to accommodate a variety of different patients and the dimensions of their interior organs and structures.

A partially enclosed lumen 310 extends from the proximal end 312 of the tubular member 302 to the curved portion 308 of the tubular member 302. The lumen 310 is sized and shaped to accommodate an ET tube and has a longitudinal opening 314 so that, after the ET tube is positioned in the trachea of the patient, the intubation assistance device 300 can be removed while the ET tube remains in place in the trachea. As such, the inner diameter of the lumen 310 is slightly larger than the outer diameter of an ET tube so that the ET tube can move axially through the lumen 310.

Attached to the proximal end 312 of the tubular member 302 is a syringe holder 332 that also serves as a grip or finger hold during insertion and removal of the device 300. Using the syringe holder 332, the ET tube and attached syringe can be pre-loaded on the device 300 for faster intubation, thus securing an airway more quickly. The syringe holder 332 can also be used to maintain positive control of the ET tube while inflating the balloon cuff on the ET tube once the tube is in place. After the cuff is inflated, the device 300 may be removed while the ET tube remains in place.

The angle of the curved portion 308 is optimized so that the proximal end 312 of the tubular member 302 may remain outside of the mouth of the patient while the distal portion 306 is angled towards the larynx of the patient. The angle of the curved portion 308 may be different in different sized devices. For example, the angle of the curved portion 308 in a pediatric device may be different from the angle of the curved portion 308 in a device intended for use on a large adult. In general, the angle 318 between the proximal portion 304 and the distal portion 306 is between 100 and 160 degrees.

The proximal end 312 of the intubation assistance device 300 remains outside of the mouth of the patient, while the distal portion 306 of the device 300 is positioned generally in the larynx of the patient. The intubation assistance device 300 further includes a foot or spacer 322 that presses against the posterior side of the hypopharynx in order to correctly position the distal portion 306 of the device 300 for intubation. The spacer 322 is attached to the distal portion 306 and the curved portion 308 of the tubular member 302. In this manner, the intubation assistance device 300 facilitates ET tube placement for establishing a definitive airway. Due to the geometry of the device 300, it is relatively easy to use to establish a direct pathway to the trachea without the use of a laryngoscope.

A ramp 324 is disposed in the distal portion 306 of the device 300 and is coextensive with the lumen 310. That is, the distal end of the lumen 310 is adjacent to the ramp 324. The ramp 324 is a relatively short, wedge-shaped protrusion that is sized and shaped to fit into the patient's vocal cords. As such, it should be well understood by a person of ordinary skill in the art that the size and shape of the ramp 324 depends upon the size of the patient in which the device 300 is used. For example, the ramp 324 in a device 300 to be used on a child will be smaller than the ramp 324 in a device 300 to be used on a large adult patient.

Below the ramp 324 is an esophageal protrusion 326 that is sized and shaped to fit within the esophagus of the patient during an intubation procedure. Compared to the ramp 324, the esophageal protrusion 326 is long and extends distally further than the ramp 324. The esophageal protrusion 326 on the distal portion 306 of the device 300 has a cylindrical shape with a tapered or flattened distal end 330. The tapered or flattened distal end 330 provides an atraumatic tip for facilitating the insertion of the esophageal protrusion 326 into the esophagus. The esophageal protrusion 326 protrudes a relatively long distance compared to the length of the ramp 324. The esophageal protrusion 326 is sized and shaped to fit in the proximal end of the patient's esophagus and/or the distal portion of the hypopharynx. As such, it should be well understood by a person of ordinary skill in the art that the size and shape of the esophageal protrusion 326 depends upon the size of the patient in which the device 300 is used. For example, the esophageal protrusion 326 in a device 300 to be used on a child will be smaller than the esophageal protrusion 326 in a device 300 to be used on a large adult patient.

A gap 328 between the ramp 324 and the esophageal protrusion 326 is sized and shaped to accommodate the tissue that lies between the esophagus and the vocal cords. For example, the gap 328 has a V-shaped surface that contacts the arytenoid area, such as the arytenoid cartilage, arytenoid muscles, and/or the interarytenoid notch that is disposed between the vocal cords and the esophagus. The gap 328 has a V-shape or a wedge shape.

The foot or spacer 322 is configured to rest against the posterior surface of the hypopharynx in order to urge the ramp 324 and the esophageal protrusion 326 into the correct location. The spacer 322 is triangular and is attached to the distal portion 306 and the curved portion 308 of the tubular member 302. As shown in the top-down view in FIG. 3D, the spacer 322 is wider than the distal portion 306 of the tubular member 302. The spacer 322 ensures a snug fit of the device 300 within the hypopharynx so that the ramp 324 and the esophageal protrusion 326 remain in place during the intubation procedure. The spacer 322 and the ramp 324 are disposed on opposite sides of the tubular member 302, with the ramp 324 disposed on top of the tubular member 302 and the spacer 322 disposed below the tubular member 302.

Figure 4A:
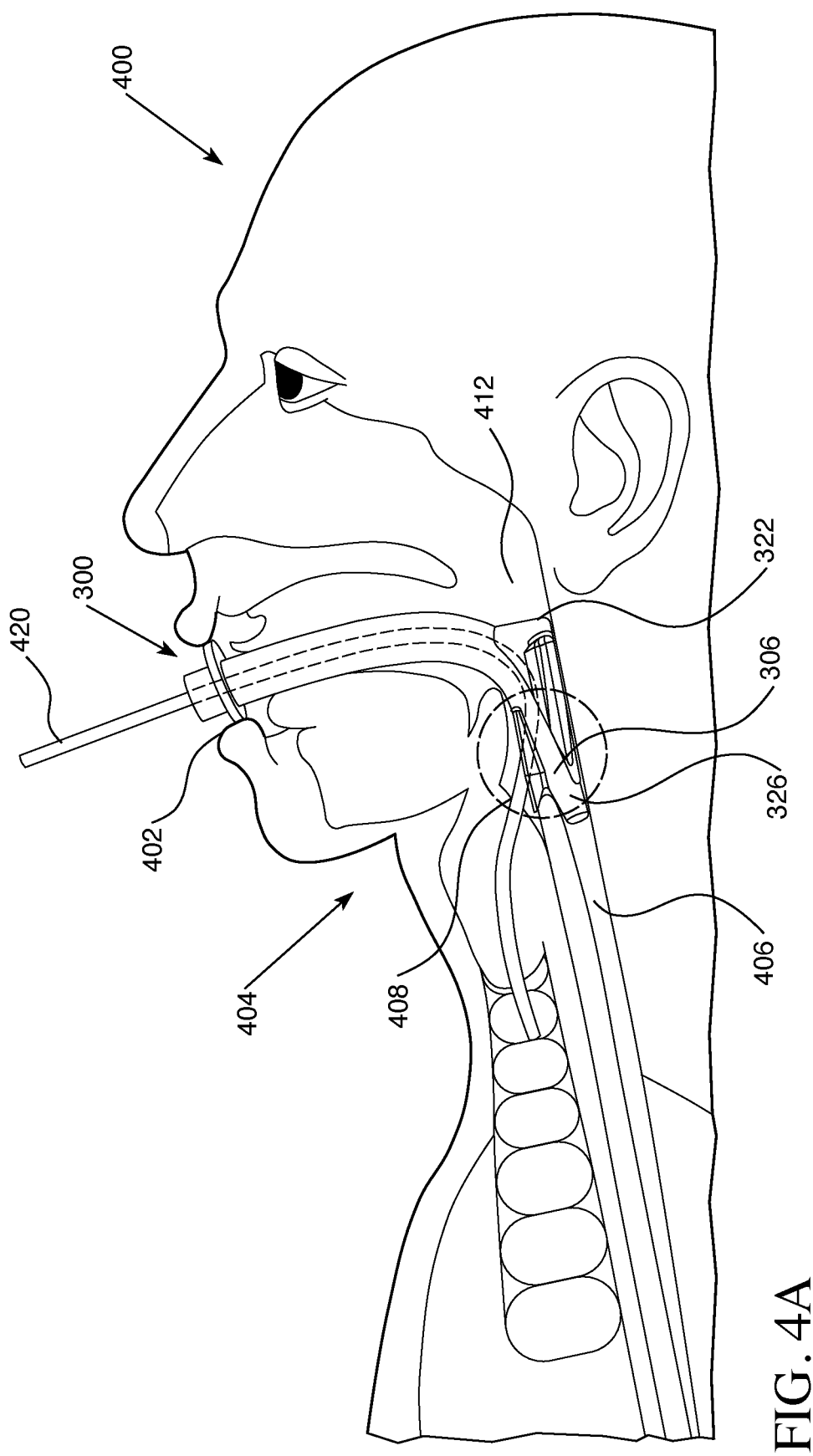
FIGS. 4A and 4B are cross-sectional views of a patient that illustrate the placement of the apparatus in FIGS. 3A-3E in the patient's airway and the placement of an ET tube in the apparatus.
Figure 4B:
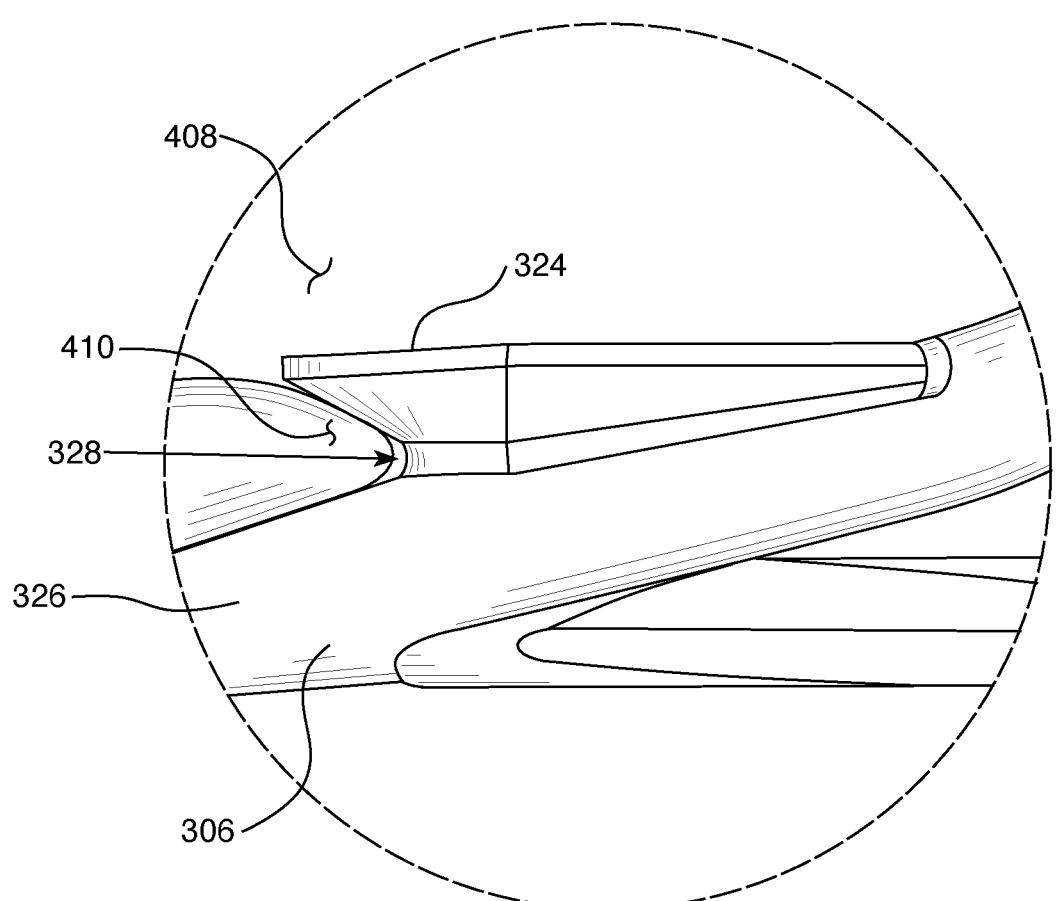

FIGS. 4A and 4B depict the intubation assistance device 300 in position in a patient 400 with the ET tube 420 inserted therethrough. The device 300 is introduced through the mouth 402 of the patient 400 and moves distally down the throat 404 until the distal portion 306 of the device 300 is properly lodged in the esophagus 406 and vocal cords 408. As shown more clearly in FIG. 4B, when the device 300 is properly positioned, the ramp 324 is disposed in the vocal cords 408 and the esophageal protrusion 326 is disposed in the esophagus 306. The wedge-shaped gap 328 between the ramp 324 and the esophageal protrusion 326 is sized and shaped to accommodate the tissue 410 that lies between the vocal cords and the esophagus. The tissue 410 includes the arytenoid area. The wedge-shaped gap 328 has a V-shaped surface that may be in contact with the arytenoid cartilage, the arytenoid muscles, and/or the interarytenoid notch. The spacer 322 of the device 300 ensures proper placement of the device 300. That is, the spacer 322 guides the device 300 into the proper position during insertion and creates a snug fit between the device 300 and the hypopharynx 412 of the patient 400. In this manner, the spacer 322 stabilizes the device 300 so that the ramp 324 and esophageal protrusion 326 remain in their correct positions during intubation.

The skilled person will be aware of a range of possible modifications of the various embodiments described above. Accordingly, the present invention is defined by the claims and their equivalents.

Additional Considerations

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a process for creating an interactive message through the disclosed principles herein. Thus, while particular embodiments and applications have been illustrated and described, it is to be understood that the disclosed embodiments are not limited to the precise construction and components disclosed herein. Various apparent modifications, changes and variations may be made in the arrangement, operation and details of the method and apparatus disclosed herein without departing from the spirit and scope defined in the appended claims.

What is claimed is:

1. An intubation assistance device for facilitating insertion of an endotracheal tube into a patient's trachea, the device comprising:
   a curved flexible tubular member comprising a proximal portion having a proximal end, a distal portion having a distal end, and a curved portion between the proximal portion and the distal portion;
   a lumen that extends from the proximal end of the tubular member and terminates in the curved portion of the tubular member, wherein the lumen is sized and shaped so that the endotracheal tube is axially moveable through the lumen;
   a ramp that is coextensive with a distal end of the lumen, wherein the ramp is configured to be inserted in between the patient's vocal cords;
   an esophageal protrusion in the distal portion of the tubular member, wherein the esophageal protrusion is configured to be inserted in the patient's esophagus; and
   a spacer attached to the distal portion and the curved portion of the tubular member, wherein the spacer has a triangular shape and is wider than the distal portion of the tubular member.

2. The device of claim 1, further comprising a gap between the ramp and the esophageal protrusion, wherein the gap is configured to accommodate tissue disposed between the vocal cords and the esophagus when the ramp is positioned in the vocal cords and the esophageal protrusion is positioned in the esophagus.

3. The device of claim 2, wherein the gap comprises a V-shaped surface configured to be in contact with at least one of: the arytenoid cartilage, arytenoid muscles, and the interarytenoid notch.

4. The device of claim 1, wherein the lumen comprises a longitudinal opening along the length of the tubular member, wherein the longitudinal opening is sized to allow an endotracheal tube disposed within the lumen to be removed through the longitudinal opening in the tubular member.

5. The device of claim 1, wherein the spacer and the ramp are disposed on opposite sides of the tubular member.

6. The device of claim 5, wherein the spacer is configured to fit within the hypopharynx of the patient.

7. The device of claim 6, wherein the spacer is configured to contact a posterior surface of the hypopharynx.

8. The device of claim 1, wherein an angle between the proximal portion and the distal portion of the tubular member is between 100 and 160 degrees.

9. The device of claim 1, wherein the esophageal protrusion extends distally farther than the ramp.

10. An intubation assistance device for facilitating insertion of an endotracheal tube or a guide wire into a patient's trachea, the device comprising:
    a curved flexible tubular member comprising a proximal portion having a proximal end, a distal portion having a distal end, and a curved portion between the proximal portion and the distal portion;
    a lumen that extends from the proximal end of the tubular member and terminates in the curved portion of the tubular member, wherein the lumen is sized and shaped so that at least one of an endotracheal tube and a guide wire is axially moveable through the lumen;
    a ramp disposed at a distal end of the lumen, wherein the ramp is angled to facilitate insertion of the at least one of the endotracheal tube and the guide wire between the vocal cords and into the patient's trachea;
    an esophageal protrusion in the distal portion of the tubular member, wherein the esophageal protrusion is configured to be inserted in the patient's esophagus; and
    a spacer attached to the distal portion and the curved portion of the tubular member, wherein the spacer and the ramp are disposed on opposite sides of the tubular member, and wherein the spacer has a triangular shape and is sized and shaped to create a snug fit between the device and the hypopharynx of the patient.

11. The device of claim 10, wherein an angle between the proximal portion and the distal portion of the tubular member is between 100 and 160 degrees.

12. The device of claim 10, wherein the ramp is a wedge-shaped protrusion that is configured to be inserted in between the patient's vocal cords.

13. The device of claim 12, further comprising a gap between the wedge-shaped protrusion and the esophageal protrusion, wherein the gap is configured to accommodate tissue disposed between the vocal cords and the esophagus when the wedge-shaped protrusion is positioned in between the vocal cords and the esophageal protrusion is positioned in the esophagus.

14. The device of claim 13, wherein the gap comprises a V-shaped surface that is sized and shaped to be in contact with at least one of: the arytenoid cartilage, the arytenoid muscles, and the interarytenoid notch.

15. The device of claim 10, wherein the lumen comprises a longitudinal opening along the length of the tubular member, wherein the longitudinal opening is sized to allow an endotracheal tube disposed within the lumen to be removed through the longitudinal opening in the tubular member.

16. The device of claim 10, wherein the ramp and the lumen are arranged so that, during an intubation procedure, the at least one of the endotracheal tube and the guide wire exits the distal end of the lumen, contacts the ramp, and passes through the vocal cords.

17. The device of claim 10, wherein the esophageal protrusion extends distally farther than the ramp.

18. The device of claim 10, wherein the ramp is coextensive with the esophageal protrusion.

19. The device of claim 10, further comprising a syringe holder attached to the proximal end of the tubular member.

20. The device of claim 10, wherein the spacer is wider than the distal portion of the tubular member.

* * * * *